United States Patent

Breuer et al.

[11] 3,932,396
[45] Jan. 13, 1976

[54] CYANOMETHYLTHIOACETYLCEPHALOSPORINS

[75] Inventors: Hermann Breuer; Uwe Treuner, both of Regensburg, Germany

[73] Assignee: E. R. Squibb & Sons, Inc., Princeton, N.J.

[22] Filed: Oct. 10, 1974

[21] Appl. No.: 513,676

Related U.S. Application Data

[62] Division of Ser. No. 278,168, Aug. 4, 1972, Pat. No. 3,855,212.

[52] U.S. Cl.... 260/243 C; 260/294.8 G; 260/326.2; 260/329 S; 260/347.2; 260/464; 260/465 D; 260/465.4; 424/246
[51] Int. Cl.$^2$............... C07D 501/36; C07D 501/26
[58] Field of Search ................................. 260/243 C

[56] References Cited
UNITED STATES PATENTS

| | | | |
|---|---|---|---|
| 3,483,197 | 12/1969 | Bickel et al. | 260/243 C |
| 3,719,673 | 3/1973 | Bickel et al. | 260/243 C |
| 3,855,212 | 12/1974 | Breuer et al. | 260/243 C |

*Primary Examiner*—Nicholas S. Rizzo
*Assistant Examiner*—Diana G. Rivers
*Attorney, Agent, or Firm*—Lawrence S. Levinson; Merle J. Smith

[57] ABSTRACT

New cyanomethylthioacetylcephalosporins of the following general formula, and their salts

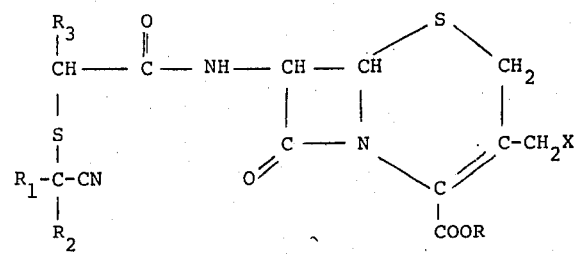

wherein R is hydrogen or a salt forming ion of the group consisting of aluminum, alkali metal, alkaline earth metal, lower alkylamine, phenyl-lower alkylamine, N,N'-dibenzylethylenediamine, procaine or lower alkylpiperidine; $R_1$ and $R_2$ each is hydrogen, lower alkyl, lower alkenyl, phenyl, hydroxyphenyl, chlorophenyl, benzyl, phenethyl or $R_1$ and $R_2$ together complete a cyclopentyl or cyclohexyl group; $R_3$ is cyclo-lower alkyl, cyclo-lower alkenyl or cyclo-lower alkadienyl; and X is hydrogen, lower alkanoyloxy, lower alkoxy or lower alkylthio.

8 Claims, No Drawings

CYANOMETHYLTHIOACETYLCEPHALOSPORINS

CROSS REFERENCE TO OTHER APPLICATIONS

This application is a division of application Ser. No. 278,168, filed Aug. 4, 1972, U.S. Pat. No. 3,855,212, Dec. 17, 1974.

SUMMARY OF THE INVENTION

This invention relates to new antibacterial cyanomethylthioacetyl cephalosporins which have the formula

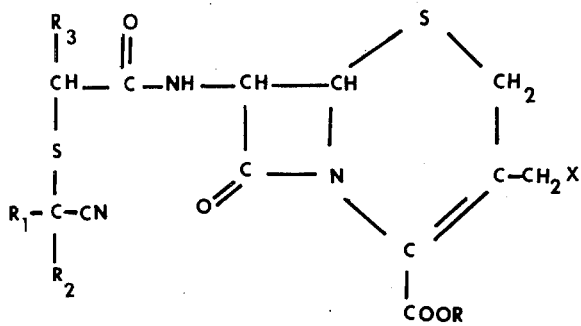

R represents hydrogen, lower alkyl aralkyl, tri(lower alkyl)silyl, a salt forming ion or the group

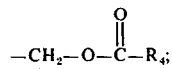

$R_1$ and $R_2$, which may be the same or different, each represents hydrogen, lower alkyl, lower alkenyl, aryl or aralkyl, each of which (other than hydrogen) may be substituted with halogen, lower alkyl or lower alkoxy; $R_1$ and $R_2$, in addition, may form a carbocyclic ring with the carbon to which they are attached; $R_3$ represents hydrogen, lower alkyl, lower alkenyl, cyclo-lower alkyl, unsaturated cyclo-lower alkyl, aryl, which may be substituted with halogen, hydroxy, amino, lower alkyl or lower alkoxy, aralkyl or certain heterocyclic groups; $R_4$ represents lower alkyl, aryl or aralkyl; X is hydrogen, hydroxy, lower alkanoyloxy, lower alkoxy, lower alkylthio, aroyloxy, aralkanoyloxy, the radical of a nitrogen base or a quaternary ammonium radical. In addition X and R may represent a bond linking carbon and oxygen in a lactone ring.

The preferred members within each group are as follows: R is hydrogen, or a salt forming ion, especially an alkali metal like sodium or potassium; $R_1$ and $R_2$ each is hydrogen, lower alkyl, especially methyl or ethyl, lower alkenyl, especially, allyl, phenyl, hydroxyphenyl, chlorophenyl, benzyl or phenethyl, most preferably $R_2$ is hydrogen when $R_1$ is other than hydrogen, and also $R_1$ and $R_2$ together complete the cyclopentyl or cyclohexyl ring; $R_3$ is hydrogen, lower alkyl, especially methyl or ethyl, lower alkenyl, especially allyl, cyclopentyl, cyclohexyl, phenyl, hydroxyphenyl, aminophenyl, chlorophenyl, benzyl, furyl, thienyl, pyrrolidyl or pyridyl; and X is hydrogen, lower alkanoyloxy, especially acetoxy, lower alkoxy, especially methoxy, lower alkylthio, especially methylthio, or pyridinium.

DETAILED DESCRIPTION OF THE INVENTION

The various groups represented by the symbols have the meanings defined below and these definitions are retained throughout this specification.

The lower alkyl groups are straight or branched chain hydrocarbon radicals having one to seven carbons in the chain, for example, methyl, ethyl, propyl, isopropyl, butyl, isobutyl, t-butyl, amyl or the like. The lower alkoxy and lower alkylthio groups contain the same radicals. The lower alkenyl groups are double bonded, monounsaturated hydrocarbon radicals of the same type, the two to four carbon members being preferred, especially allyl.

The cyclo-lower alkyl groups included cycloaliphatic groups having four to seven carbons in the ring as cyclobutyl, cyclopentyl, cyclohexyl and cycloheptyl. The cyclic groups may also be unsaturated, e.g., cycloalkenyl and cycloalkadienyl groups of the same type, e.g., cyclobutenyl, cyclopentenyl, cyclohexenyl, cyclopentadienyl, cyclohexadienyl, etc. The double bond or bonds may be variously located. A preferred radical is the 1,4-cyclohexadienyl group.

The foregoing may by simply substituted as defined above, with one to three groups such as halogen, hydroxy, amino, lower alkyl or lower alkoxy, preferably only one substituent.

The aryl groups are phenyl and simply substituted phenyl containing one to three substituents (preferably only one) as defined above. The aralkyl groups include phenyl-lower alkyl and those similarly substituted on the phenyl ring as defined above.

The lower alkanoyloxy, aroyloxy and aralkanoyloxy groups represented by X include the acyl group of acid esters. The lower alkanoyl radicals are the acyl radicals of lower fatty acids containing alkyl radicals of the type described above. The lower alkanoyloxy groups include, for example, acetoxy, propionyloxy, butyryloxy and the like. The aroyloxy groups are benzoyloxy and the aralkanoyloxy groups consisting of phenyl-lower alkanoyloxy radicals of the type described. X also represents the radical of an amine, e.g., a lower alkylamine like methylamine, ethylamine, dimethylamine, triethylamine, phenyl-lower alkylamine like dibenzylamine, phenyl-lower alkylpyridinium like N,N'-dibenzylpyridinium, pyridinium, 1-quinolinium, 1-picolinium, etc. X and R may also join together, as indicated above, to form a bond linking carbon and oxygen in a lactone ring.

The heterocyclic groups represented by $R_3$ are 5- to 6-membered monocyclic heterocyclic radicals (exclusive of hydrogen) containing nitrogen, sulfur or oxygen in the ring in addition to carbon (not more than two hetero atoms), and members of this group simply substituted as discussed above with respect to the phenyl groups. The heterocyclic radicals include pyridyl, pyrrolidyl, morpholinyl, thienyl, furyl, oxazolyl, isoxazolyl, thiazolyl and the like, as well as the simply substituted members, especially the halo, lower alkyl (particularly methyl and ethyl), lower alkoxy (particularly methoxy and ethoxy), phenyl and hydroxy-lower alkyl (particularly hydroxymethyl and hydroxyethyl) substituted members.

The salt forming ions may be metal ions, e.g., aluminum, alkali metal ions such as sodium or potassium, alkaline earth metal ions such as calcium or magnesium, or an amine salt ion, of which a number are known for this purpose, for example, aralkylamine like, dibenzylamine, N,N-dibenzylethylenediamine, lower alkylamine like methylamine, triethylamine, procaine, lower alkylpiperidine like N-ethylpiperidine, etc.

The compounds of formula I are produced by acylating a compound of the formula

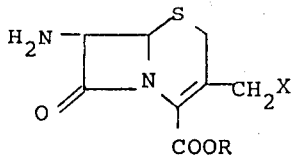
COOR wherein X and R have the meaning defined above, with a reactive derivative of an acid of the formula (III)
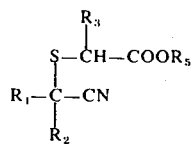

wherein $R_1$, $R_2$ and $R_3$ have the meaning defined above and $R_5$ in this case is hydrogen.

The reactive derivatives of the acids of formula III include, for example, acid halides, acid anhydrides, mixed anhydrides of the acid with carbonic acid monoesters, trimethylacetic acid or benzoic acid, acid azides, active esters like cyanomethyl ester, p-nitrophenyl ester or 2,4-dinitrophenylester, or active amides like acylimidazoles.

An acid of formula III may also be reacted with a compound of formula II in the presence of a carbodiimide, for example, N,N-dicyclohexylcarbodiimide, an isoxazolium salt, for example, N-ethyl-5-phenylisoxazolium-3-sulfonate or 2-ethoxy-1,2-dihydroquinoline-1-carboxylic acid ester.

The acids of formula III and their ester of formula VI are new compounds which may be produced from the corresponding derivatives of haloacetonitriles having the formula (IV)
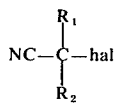

wherein $R_1$ and $R_2$ have the meaning defined above and hal is halogen, especially chlorine, by reaction with a thioacetic acid ester of the formula (V)
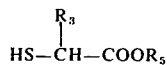

wherein $R_3$ has the meaning defined above and $R_5$ here is lower alkyl, especially methyl or ethyl, in the presence of an acid binding agent. The ester formed by this reaction has the formula (VI)
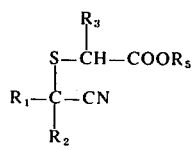

and this is converted, at the conclusion of that reaction, to the free acid of formula III by conventional saponification.

Alternatively, acids of formula III, i.e., wherein $R_5$ is hydrogen may be produced directly by reacting a haloacetonitrile of formula IV with a thioacetic acid of formula V, i.e., $R_5$ is hydrogen in formula V, in the presence of a base, e.g., an alkylamine like triethylamine.

An alternate process for the production of a compound of formula III is by the reaction of a thioacetonitrile of the formula (VII)
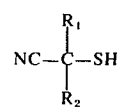

with a haloacetic acid of the formula (VIII)
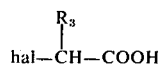

wherein hal is halogen, preferably chlorine, in the presence of an acid binding agent.

Another route for the synthesis of the esters of formula III, i.e., wherein $R_5$ is lower alkyl, is by converting an ester of halomethylmercaptoacetic acid [C.A. 58, 5630 (1963)] with cyanide as follows:

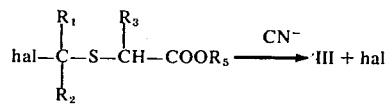

When R is the acyloxymethyl group

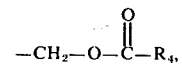

this group may be introduced onto the 7-aminocephalosporanic acid moiety either prior to or subsequent to the reaction with the acylating agent by treatment with one or two moles of a halomethyl ester of the formula hal—CH$_2$OCOR$_4$   (IX)

wherein hal is halogen, preferably chlorine or bromine, in an inert organic solvent such as dimethylformamide, acetone, dioxane, benzene or the like at about ambient temperature or below.

The products of this invention form salts which are also part of the invention. Basic salts form with the acid moiety as discussed above when the symbol R is hydrogen.

It will be appreciated that certain of the compounds of this invention exist in various states of solvation as well as in different isomeric or optically active forms. The various forms as well as their mixtures are within the scope of this invention.

Further process details are provided in examples.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes.* They may be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

The following examples are illustrative of the invention. All temperatures are on the centigrade scale. Additional variations may be produced in the same manner by appropriate substitution in the starting material.

EXAMPLE 1

2-[(Cyanomethyl)thio]acetic acid methyl ester 31.8 G. (0.3 mol) of thioacetic acid methyl ester are added to 150 ml. (0.3 mol.) of 2N sodium methylate solution. 22.6 g. (0.3 mol.) of chloroacetonitrile dissolved in 30 ml. of methanol are added dropwise while cooling and stirring. It is stirred overnight then refluxed for 30 minutes. The reaction mixture is cooled and the solvent is evaporated. 100 ml. of water are added to the residue and the aqueous solution is extracted twice with ether. The combined ether extracts are decolorized with activated carbon and dried with magnesium sulfate. The ether is distilled off and the residue is distilled under vacuum. 30.5 g. of 2-[(cyanomethyl)thio]acetic acid methyl ester are obtained b.p.$_{10mm}$ 132°–134°.

EXAMPLE 2

2-[(Cyanomethyl)thio]acetic acid potassium salt 14.5 G. (0.1 mol.) of 2-[(cyanomethyl)thio]acetic acid methyl ester are dissolved in ethanol and a solution of 6.7 g. (0.12 mol.) of potassium hydroxide in 40 ml. of ethanol is added dropwise while cooling. This is stirred 4 hours at room temperature and 1 hour at 0°. The resulting precipitate is filtered under suction, washed with ethanol and ether and dried. 15.4 g. of 2-[(cyanomethyl)thio]acetic acid, potassium salt, m.p. 203°–205° (dec.) are obtained. The free acid is obtained by dissolving the potassium salt in water and treating with an equivalent amount of aqueous sulfuric acid. The ether solution is dried and concentrated to obtain the free acid.

EXAMPLE 3

2-[(Cyanomethyl)thio]acetyl chloride

30 G. of 2-[(cyanomethyl)thio]acetic acid potassium salt are suspended in benzene, 5 drops of pyridine are added and the mixture is cooled to 10°. At this temperature 76.7 g. of oxalyl chloride in 150 ml. of benzene are slowly dropped in with stirring. After the vigorous evolution of gas has stopped, the reaction mixture is stirred for 1 hour at room temperature. This is then filtered and the filtrate is concentrated at room temperature. The residue is distilled under vacuum to obtain 19.8 g. of 2-[(cyanomethyl)thio]acetyl chloride, b.p. $_{0.1mm}$ 110°–115°.

EXAMPLE 4

7-[2-[(Cyanomethyl)thio]acetamido]-3-desacetoxycephalosporanic acid 2.14 G. (0.01 mol.) of 7-amino-3-desacetoxycephalosporanic acid are suspended in 50 ml. of water at room temperature. 1.4 ml. of triethylamine salt are added and this is stirred until a clear solution is obtained. 50 ml. of acetone are added and the solution is cooled to 0°–5°. Simultaneously a solution of 1.65 g. (0.01 mol.) of 2-[(Cyanomethyl)thio]acetyl chloride in 15 ml. of acetone and a solution of 1.4 ml. of triethylamine in 15 ml. of acetone are added dropwise while stirring with care that the pH stays in the range 7.5–8. This is stirred for an additional 30 minutes at 5°. Then 50 ml. of ethyl acetate are added, cooled to 0° and acidified with 2N hydrochloric acid to pH1.5. The mixture is filtered, the layers are separated, the organic phase is washed three times with water, dried with magnesium sulfate and the solvent is evaporated in a rotary evaporator. 1.9 g. of 7-[2-[(cyanomethyl)]thio]acetamido-3-desacetoxycephalosporanic acid are obtained. The crude product is dissolved in methanol, filtered and 5 ml. of a 2N solution of potassium ethylhexanoate in n-butanol are added. This solution is poured into 300 ml. of ether. The precipitate is filtered under suction and washed with ether.

The yield amounts to 1.8 g. of the potassium salt of 7-[2-[(cyanomethyl)thio]acetamido]-3-desacetoxycephalosporanic acid, m.p. 175° (dec.). The amorphous product is crystallized from a little methanol, m.p. 197°–200° (dec.).

EXAMPLE 5

7-[2-[(Cyanomethyl)thio]acetamido]-cephalosporanic acid

By substituting 7-aminocephalosporanic acid for the 7-amino-3-desacetoxycephalosporanic acid in the procedure of Example 4, there are obtained 7-[2[-(cyanomethyl)thio]acetamido]cephalosporanic acid and the crystalline potassium salt, m.p. 168°–170° (dec.).

EXAMPLE 6

To obtain the triethylamine salt of 7-[2-[(cyanomethyl)thio]acetamido]cephalosporanic acid, an equivalent amount of triethylamine is added to an ethanol solution of 7-[2-[(cyanomethyl)thio]acetamido]cephalosporanic acid and the reaction product is concentrated at reduced pressure to deposit the product.

The following additional products are obtained according to the procedure of Example 4 by substituting for the 2-[(cyanomethyl)thio]acetyl chloride the appropriately substituted derivative and substituting for the 7-ADCA the appropriately substituted derivative:

TABLE

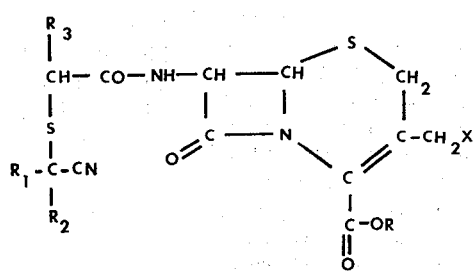

| Ex. | R | R₁ | R₂ | R₃ | X |
|---|---|---|---|---|---|
| 7 | H | H | H | 3-NH₂-C₆H₄- | H |
| 8 | CH₃ | CH₃ | H | H | H |
| 9 | C₂H₅ | C₂H₅ | C₂H₅ | CH₃ | OH |
| 10 | K | C₂H₅ | H | C₃H₇ | pyridinium |
| 11 | -CH₂OC(O)-CH(CH₃)₂ | H | H | C₆H₅CH₂- | OCOCH₃ |
| 12 | -CH₂OC(O)-C₆H₅ | CH₂-CH=CH₂- | H | 4-ClC₆H₄- | OCOCH₃ |
| 13 | K | 4-CH₃O-C₆H₄- | H | 3,4-(CH₃O)₂C₆H₃- | H |
| 14 | C₂H₅ | CH₃ | CH₃ | 3,4,5-(CH₃O)₃C₆H₂- | OCOCH₃ |
| 15 | H | -CH₂C₆H₅ | -CH₂C₆H₅ | 4-CH₃C₆H₄- | OCOCH₃ |
| 16 | lactone (+X) | C₂H₅ | H | 3,4-(Br)₂C₆H₃- | lactone (+R) |
| 17 | K | 4-Cl-C₆H₄- | H | 2,4-(Cl)₂C₆H₃- | OCOCH₃ |
| 18 | K | H | H | 3-C₆H₅-5-CH₃-isoxazol-4-yl | OCOCH₃ |
| 19 | C₂H₅ | -CH₂CH₂C₆H₅ | H | morpholino- | OCOCH₃ |
| 20 | Na | H | H | 3-CH₃-pyridin-6-yl | OCOCH₃ |
| 21 | C₂H₅- | CH₃ | H | thien-2-yl | OCOCH₃ |
| 22 | C₆H₅CH₂- | -CH₂C₆H₅ | H | fur-2-yl | OOCH₂C₆H₅ |

TABLE-continued

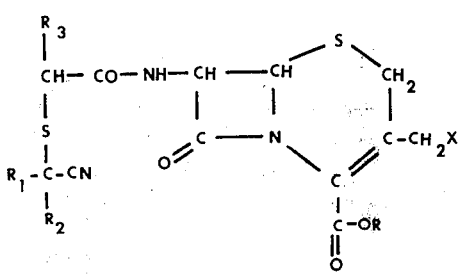

| Ex. | R | $R_1$ | $R_2$ | $R_3$ | X |
|---|---|---|---|---|---|
| 23 | $-CH_2O\overset{O}{\overset{\|}{C}}-CH(CH_3)_2$ | $-CH_2OH$ | $C_2H_5$ | $C_6H_5-H$ | |
| 24 | $-CH_2O-\overset{O}{\overset{\|}{C}}-CH(CH_3)_2$ | 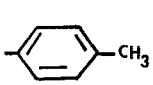 | H | $C_2H_5-$ | $-OOC-C_6H_5$ |
| 25 | H |  | | $C_6H_5-$ | H |
| 26 | Na |  | | $C_2H_5-$ | H |
| 27 | $-CH_2O-\overset{O}{\overset{\|}{C}}-CH(CH_3)_2$ |  | | $C_6H_5-$ | $-OCOCH_3$ |
| 28 | $-Si(CH_3)_3$ | $-CH_2-CH=CH_2$ | H | $C_2H_5-$ | H |
| 29 | $-N(C_2H_5)_3$ | $CH_3$ | H | $C_6H_5-$ | H |
| 30 | Na |  | H | $C_6H_5-$ | $-OCOCH_3$ |
| 31 | K | H | H |  | $-SCH_3$ |
| 32 | H | H | H |  | $-OCH_3$ |
| 33 | $-CH_2O\overset{O}{\overset{\|}{C}}C_6H_5$ | H | H | 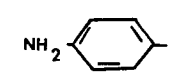 | H |
| 34 | K | $CH_3$ | $CH_3$ | $CH_2=CH-CH_2-$ | H |
| 35 | H | H | H | $CH_3CH=CH-CH_2-$ | $-OCOCH_3$ |
| 36 | H | H | H | $CH_2=CH-CH_2-CH_2-$ | $OCOCH_3$ |
| 37 | K | $C_2H_5$ | H |  | H |

TABLE-continued

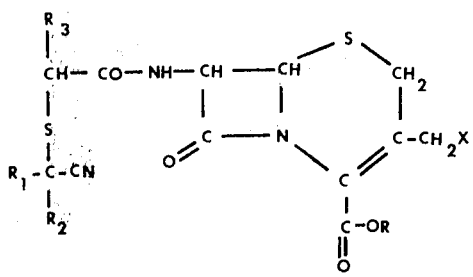

| Ex. | R | R₁ | R₂ | R₃ | X |
|-----|---|-----|-----|-----|---|
| 38 | H | H | H | $CH_2=CH-CH_2-$ | $OCOCH_3$ |
| 39 | K | $CH_3$ | H | cyclopentyl-H | H |
| 40 | H | H | H | cyclopentyl-H | pyridinium |
| 41 | K | $C_2H_5$ | H | $CH_3-N\langle\rangle-$ | H |
| 42 | H | H | H | phenyl- | $OCOCH_3$ |
| 43 | K | H | H | phenyl- | H |
| 44 | H | H | H | phenyl- | $OCOCH_3$ |
| 45 | H | $CH_3$ | H | $HO-\langle\rangle-$ | H |

EXAMPLE 46

A sterile powder for reconstitution for use intramuscularly is prepared from the following ingredients which supply 1000 vials each containing 250 mg. of active ingredient:

| | |
|---|---|
| 7-[2-[(cyanomethyl)thio]acetamido]-cephalosporanic acid, sterile | 250 gm. |
| Lecithin powder, sterile | 50 gm. |
| Sodium carboxymethylcellulose, sterile | 20 gm. |

The sterile powders are aseptically blended and filled into sterile vials, and sealed. The addition of 1 ml. of water for injection to the vial provides a suspension for intramuscular injection.

EXAMPLE 47

DL-2-[(cyanomethyl)thio]-2-phenyl Acetic Acid 16.8 Gms. (0.1 mol.) of DL-2-phenylthioacetic acid and 22.7 gms. (0.225 mol.) of triethylamine are dissolved in 200 ml. of anhydrous tetrahydrofuran. The solution is cooled to 0° to 5° and a solution of 7.54 gms. (0.1 mol.) of chloroacetonitrile is added dropwise at this temperature. The mixture is stirred at 0° to 5° for 3 hours and then kept overnight at room temperature. The solution is concentrated, the residue is taken up with water, acidified with 2N hydrochloric acid and extracted several times with ether. The ether extracts are washed with water, dried with magnesium sulfate and concentrated. The residue crystallizes to yield 20.6 gms. of DL-2-[(cyanomethyl)thio]-2-phenyl acetic acid, m.p. 110°–112°. After recrystallization from benzene, the acid melts at 114°.

EXAMPLE 48

7-[DL-2-[(cyanomethyl)thio]-2-phenylacetamido]-cephalosporanic acid 1.1 Gm. (.0054 mol.) of 7-[DL-2-(cyanomethyl)thio]-2-phenyl acetic acid are dissolved in 12.5 ml. of dioxane. A solution of 0.98 gms. of 2,4-dinitrophenol in 12.5 ml. of dioxane is added, the mixture is cooled with ice water and 1.08 gms. of dicyclohexylcarbodiimide are added. This is stirred for 30 minutes with cooling and 30 minutes at room temperature, and the resulting precipitate (dicyclohexylurea, 1.1 gm.) is filtered under suction. The filtrate is concentrated at room temperature under vacuum. To the oily residue is added with cooling a solution prepared from 1.36 gms. (0.05 mols.) of 7-aminocephalosporanic acid and 1.06 gms. of triethylamine in 12.5 ml. of methylene chloride. The mixture is stirred for 16 hours at room temperature.

A slight turbidity is removed by filtration and the solution is slowly added to 200 ml. of cold, vigorously stirred ether. After filtering under suction, the residue is dissolved in a small amount of methylene chloride and reprecipitated in the same manner as described above. The yield amounts to 1.7 gms. of the triethylamine salt of 7-[DL-2-[(cyanomethyl)thio]-2-phenylacetamido]cephalosporanic acid. A sample of the product shows only a trace of dinitrophenol by thin layer chromatography.

To produce the free acid, 1.6 gms. of the triethylamine salt are dissolved in 40 ml. of water, layered over with ethyl acetate and acidified with 2N hydrochloride while cooling and stirring. The layers are separated, the aqueous layer is extracted several times with ethyl acetate, the combined extracts are washed three times with water, decolorized with activated charcoal, dried with magnesium sulfate and then the solution is evaporated to dryness. The viscous residue is dissolved in 25 ml. of methylene chloride and the solution is poured into 200 ml. of vigorously stirred petroleum ether. 0.9 gms. of 7-[DL-2-[(cyanomethyl)thio]-2-phenylacetamido]-cephalosporanic acid precipitate.

The potassium salt is produced by dissolving 0.8 gms. of the acid in 10 ml. of methanol and to this is added 1.25 ml. of a 2N solution of ethyl hexanoate in n-butanol. A light turbidity is filtered off and the solution is slowly poured into 200 ml. of vigorously stirred ether. There are obtained 0.75 gms. of the potassium salt, m.p. below 60° (dec.).

What is claimed is:

1. A compound of the formula

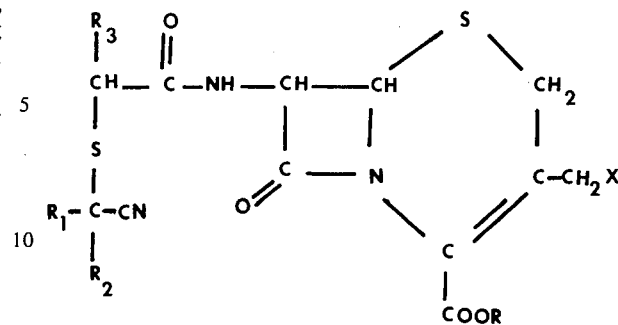

wherein R is hydrogen or a salt forming ion of the group consisting of aluminum, alkali metal, alkaline earth metal, mono-lower alkylamine; dilower alkylamine, tri-lower alkylamine, dibenzylamine, N,N'-dibenzyl- ethylenediamine, procaine or lower alkylpiperidine; $R_1$ and $R_2$ each is hydrogen, lower alkyl, lower alkenyl, phenyl, hydroxyphenyl, chlorophenyl, benzyl, phenethyl or $R_1$ and $R_2$ together complete the cyclopentyl or cyclohexyl group; $R_3$ is $C_4$–$C_7$-cyclolower alkyl, $C_4$–$C_7$-cyclo-lower alkenyl or $C_4$–$C_7$-cyclolower alkadienyl; and X is hydrogen, lower alkanoyloxy, lower alkoxy or lower alkylthio; said lower alkyl, lower alkenyl, lower alkanoyloxy and lower alkoxy groups having up to seven carbon atoms.

2. A compound as in claim 1 wherein $R_3$ is cyclolower alkadienyl.

3. A compound as in claim 2 wherein the cyclo-lower alkadienyl group is cyclohexadienyl.

4. A compound as in claim 1 wherein R is hydrogen or alkali metal, $R_1$ and $R_2$ each is hydrogen, $R_3$ is cyclohexadienyl and X is hydrogen or acetoxy.

5. A compound as in claim 4 wherein R is hydrogen and X is acetoxy.

6. A compound as in claim 4 wherein R is potassium and X is hydrogen.

7. A compound as in claim 1 wherein R is potassium, $R_1$ is ethyl, $R_2$ and X each is hydrogen and $R_3$ is cyclohexyl.

8. A compound as in claim 1 wherein R, $R_1$ and $R_2$ each is hydrogen, $R_3$ is cyclohexenyl and X is acetoxy.

* * * * *